United States Patent
Aoki et al.

(10) Patent No.: US 9,487,484 B2
(45) Date of Patent: Nov. 8, 2016

(54) STILBAZOLIUM DERIVATIVE AND NONLINEAR OPTICAL MATERIAL USING THE SAME

(71) Applicants: ARKRAY, Inc., Kyoto (JP); National University Corporation Yamagata University, Yamagata (JP)

(72) Inventors: Kazuyoshi Aoki, Kyoto (JP); Shuji Okada, Yamagata (JP)

(73) Assignees: Arkray, Inc., Kyoto-shi, Kyoto (JP); National University Corporation Yamagata University, Yamagata-shi, Yamagata (JP)

(*) Notice: Subject to any disclaimer, the term of this patent is extended or adjusted under 35 U.S.C. 154(b) by 0 days.

(21) Appl. No.: 14/748,050

(22) Filed: Jun. 23, 2015

(65) Prior Publication Data
US 2016/0016905 A1  Jan. 21, 2016

(30) Foreign Application Priority Data
Jun. 24, 2014  (JP) .................................. 2014-129498

(51) Int. Cl.
| | | |
|---|---|---|
| C07D 213/38 | (2006.01) | |
| C07D 413/10 | (2006.01) | |
| G02F 1/13 | (2006.01) | |
| C07C 309/35 | (2006.01) | |
| C07C 309/39 | (2006.01) | |
| C07C 309/40 | (2006.01) | |
| C09K 11/06 | (2006.01) | |
| G02F 1/35 | (2006.01) | |
| G02F 1/355 | (2006.01) | |
| G02F 1/37 | (2006.01) | |

(52) U.S. Cl.
CPC ............ *C07D 213/38* (2013.01); *C07C 309/35* (2013.01); *C07C 309/39* (2013.01); *C07C 309/40* (2013.01); *C07D 413/10* (2013.01); *C09K 11/06* (2013.01); *G02F 1/13* (2013.01); *G02F 1/3534* (2013.01); *G02F 1/3551* (2013.01); *G02F 1/37* (2013.01); *C09K 2211/1048* (2013.01)

(58) Field of Classification Search
CPC ......................... C07D 213/38; C07D 413/10
See application file for complete search history.

(56) References Cited

U.S. PATENT DOCUMENTS

2007/0023739 A1  2/2007 Izumi et al.
2012/0193554 A1  8/2012 Uchida

FOREIGN PATENT DOCUMENTS

| JP | 2012-177896 A | 9/2012 |
| WO | 2005071145 A1 | 8/2005 |
| WO | WO 2007/110532 A2 | 10/2007 |

OTHER PUBLICATIONS

Vasilev, et al. Document No. 150:146346, retrieved from CAPLUS; entered in STN on Dec. 5, 2007.*
Choi, D. H. et al., "Second-order nonlinear optical properties of novel α-methylstyrene copolymers containing the organo-boron salt dye chromophore in the side chain", Synthetic Metals 71:1731-1732 (1995).
Vasilev, Aleksey et al., "Novel environmentally benign procedures for the synthesis of styryl dyes", Dyes and Pigments, 77:550-555 (2008).
Krieg, R. et al., "N,N-Dialkylaminostyryl dyes: specific and highly fluorescent substrates of peroxidase and their application in histochemistry", Journal of Molecular Histology, 39:169-191 (2008).
Choi, Dong Hoon et al., "Synthesis of second-order nonlinear optical polymers containing stilbazolium salt chromophore in the side chain", Molecular Crystals and Liquid Crystals, 267:53-58 (1995).
Extended European Search Report issued in Application No. 15173358.1 on Oct. 20, 2015.

* cited by examiner

*Primary Examiner* — Shawquia Jackson
(74) *Attorney, Agent, or Firm* — Knobbe Martens Olson & Bear LLP

(57) ABSTRACT

Provided is a stilbazolium derivative represented by the general formula (I):

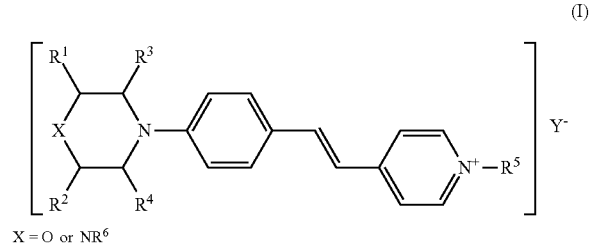

wherein $R^1$, $R^2$, $R^3$, and $R^4$ independently represent hydrogen, halogen, alkyl, hydroxyl, carboxyl, or amino; $R^5$ represents hydrogen or alkyl; X represents oxygen or $NR^6$ ($R^6$ is hydrogen or alkyl); and $Y^-$ represents an anion. In the general formula (I), some or all of hydrogens maybe deuterium.

20 Claims, 4 Drawing Sheets

STILBAZOLIUM DERIVATIVE AND NONLINEAR OPTICAL MATERIAL USING THE SAME

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

This application claims priority to and the benefit of Japanese Patent Application No. 2014-129498 filed in the Japanese Intellectual Property Office on Jun. 24, 2014, the entire contents of which are incorporated herein by reference.

BACKGROUND OF THE INVENTION

1. Field of the Invention

The present invention relates to novel stilbazolium derivatives useful as nonlinear optical materials.

2. Description of the Related Art

Conventionally, inorganic nonlinear optical materials such as $LiNbO_3$ (LN) have been used as electro-optical (EO) materials for electro-optical (EO) elements. However, as a result of research for organic materials exhibiting great nonlinear optical properties, an organic nonlinear optical material DAST useful as an EO material has been recently used as described in WO 2005/071145.

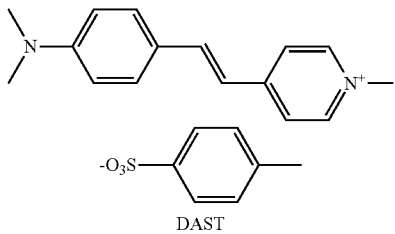

DAST

SUMMARY OF THE INVENTION

The absorption edge of DAST is present at around 720 nm. When DAST is used as a nonlinear optical material for a 1.3 μm band, there is a problem that DAST absorbs light of around 650 nm subsidiarily generated by second harmonic generation (SHG), resulting in degradation of the material. Accordingly, properties required for a nonlinear optical material are that the nonlinear optical material has great optical nonlinearity and that the nonlinear optical material does not have absorption in a longer wavelength side than the wavelength region of a second harmonic.

Thus, an objective of the present invention is to provide an organic nonlinear optical material that exhibits great optical nonlinearity and does not have absorption in the long wavelength region of visible light. In addition, the present invention is directed at providing a novel nonlinear optical material that has an absorption edge ($\lambda_{CUTOFF}$) present in a shorter wavelength of 600 nm or less and has higher second-order nonlinear optical activity, compared with conventional stilbazolium nonlinear optical materials represented by DAST.

In one aspect, the present invention provides a stilbazolium derivative represented by the following general formula (I):

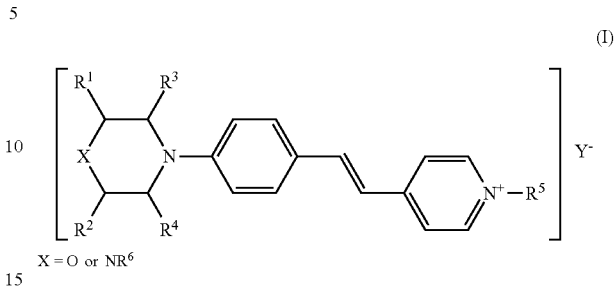

wherein $R^1$, $R^2$, $R^3$, and $R^4$ independently represent hydrogen, halogen, alkyl, hydroxyl, carboxyl, or amino; $R^5$ represents hydrogen or alkyl; X represents oxygen or $NR^6$ ($R^6$ is hydrogen or alkyl); and $Y^-$ represents an anion. In the general formula (I), some or all of hydrogens may be deuterium.

In another aspect, the present invention provides a nonlinear optical material comprising the stilbazolium derivative represented by the general formula (I) as well as a light source device and a terahertz wave generation device in which the nonlinear optical material is used.

In the present invention, the term "nonlinear optical material" includes "EO material".

When the nonlinear optical material of the present invention is used as a nonlinear optical material for a 1.3 μm band, the absorption edge of the nonlinear optical material shifts to a shorter wavelength side than that of DAST. Therefore, absorption does not occur in the vicinity of 650 nm which is the wavelength of a second harmonic, degradation as a nonlinear optical material is inhibited, and a longer life is expected.

With regard to a second-order nonlinear optical property, a first molecular hyperpolarizability β is $242 \times 10^{-30}$ esu (calculated by the MOPAC/PM5 method which is the semiempirical molecular orbital method) in the cation portion of DAST, whereas a hyperpolarizability β is $279 \times 10^{-30}$ esu in the cation portion of the stilbazolium derivative having a morpholine skeleton of the present invention, and a hyperpolarizability β is $289 \times 10^{-30}$ esu in the cation portion of the stilbazolium derivative having a piperazine skeleton. Since the property on a molecular level is improved, the nonlinear optical material of the present invention is considered to be a very useful nonlinear optical material.

DETAILED DESCRIPTION OF THE PREFERRED EMBODIMENT

Figure 1:
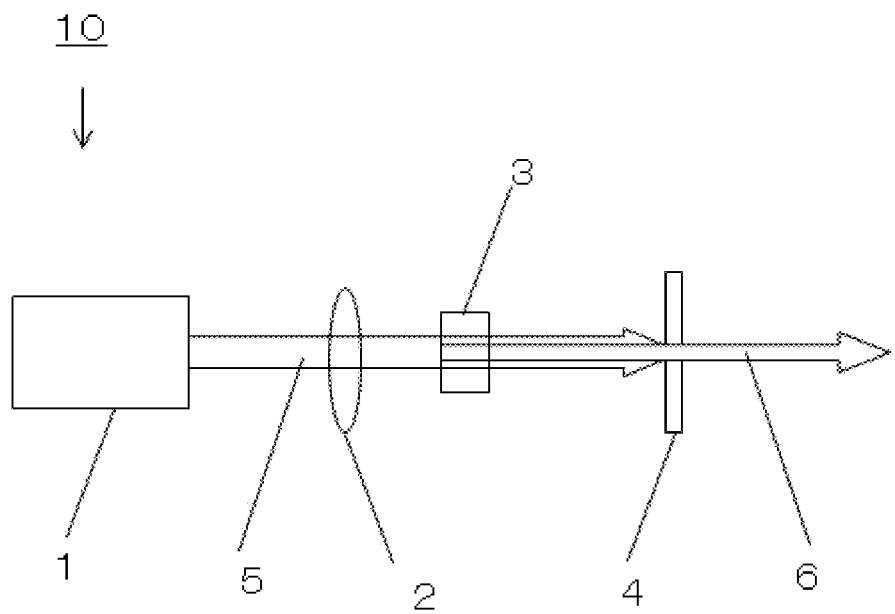
FIG. 1 is a schematic view of a light source device according to one embodiment of the present invention.

In the stilbazolium derivative of the present invention, a morpholine skeleton or a piperazine skeleton is bound to a stilbazolium skeleton as represented by the following general formula (I):

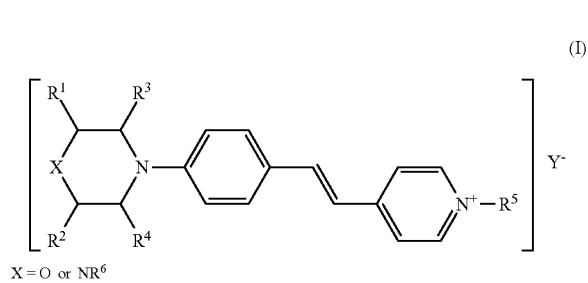

wherein $R^1$, $R^2$, $R^3$, and $R^4$ independently represent hydrogen, halogen, alkyl, hydroxyl, carboxyl, or amino; $R^5$ represents hydrogen or alkyl; X represents oxygen or $NR^6$ ($R^6$ is hydrogen or alkyl); and $Y^-$ represents an anion. In the general formula (I), a compound in which some or all of hydrogens are substituted by deuterium is also encompassed.

$R^1$ and $R^2$ are more preferably hydrogen or alkyl, $R^3$ and $R^4$ are more preferably hydrogen, and $R^5$ is more preferably alkyl.

Examples of halogen include F, Cl, Br, and I.

Examples of alkyl include $C_1$-$C_{10}$, more preferably $C_1$-$C_5$, straight or branched chain alkyl, specifically, methyl, ethyl, n- or i-propyl, n- or i-butyl, n- or i-pentyl, and neopentyl. Especially, methyl or ethyl is preferable. A hydrogen atom of the alkyl group may be substituted. Examples of such a substituent include functional groups such as a halogen atom, hydroxyl group, ether group, carboxyl group, ester group, nitro group, amino group, and sulfone group.

$Y^-$ is not particularly limited if being a group exhibiting anionic properties. Examples of $Y^-$ include anions of halogen atoms such as F, Cl, Br, and I, sulfonic acid anions, and carboxylic acid anions. Examples of the sulfonic acid anions include benzenesulfonic acid anions represented by the structural formula described below. A hydrogen sulfate ion, a nitrate ion, a tetrafluoroborate ion, a perchlorate ion, a perbromate ion, and a periodate ion are also exemplified.

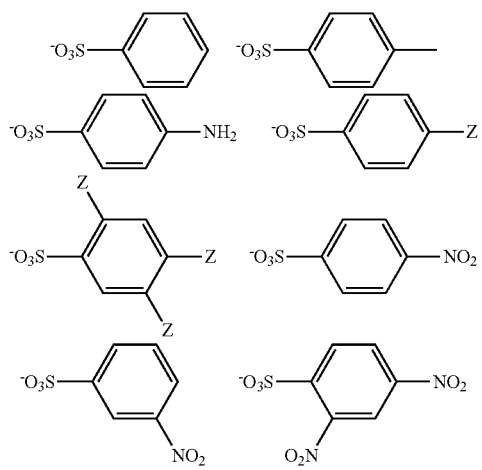

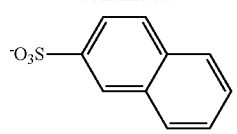

In the structural formula, Z represents halogen.

More preferred examples of the stilbazolium derivative of the present invention include a compound represented by the following general formula (II):

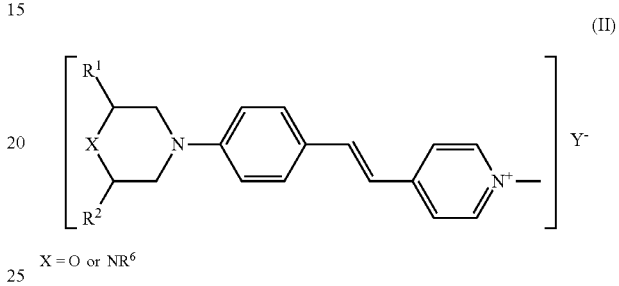

wherein $R^1$ and $R^2$ independently represent hydrogen or alkyl; X represents oxygen or $NR^6$ ($R^6$ is hydrogen or alkyl); and $Y^-$ represents an anion. In the general formula (II), a compound in which some or all of hydrogens are substituted by deuterium is also encompassed.

In this case, $R^1$ and $R^2$ are preferably alkyl when X is oxygen, and $R^1$ and $R^2$ are preferably hydrogen when X is $NR^6$ ($R^6$ is hydrogen or alkyl).

The stilbazolium compound having a morpholine skeleton and the stilbazolium compound having a piperazine skeleton, represented by the general formula (I), of the present invention can be synthesized by, for example, a synthetic pathway described below.

Synthesis of Stilbazolium Compound

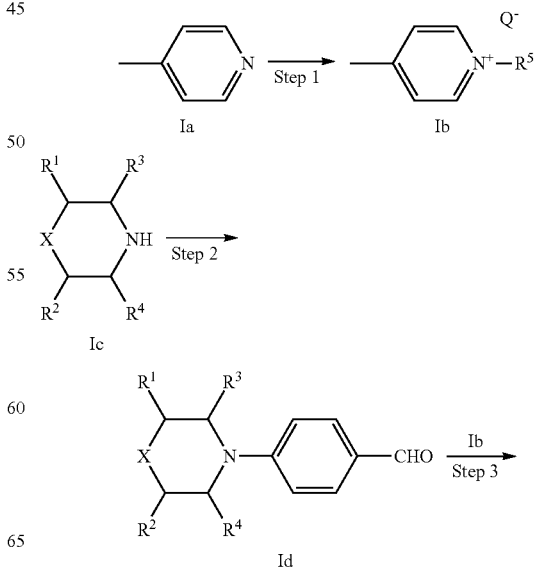

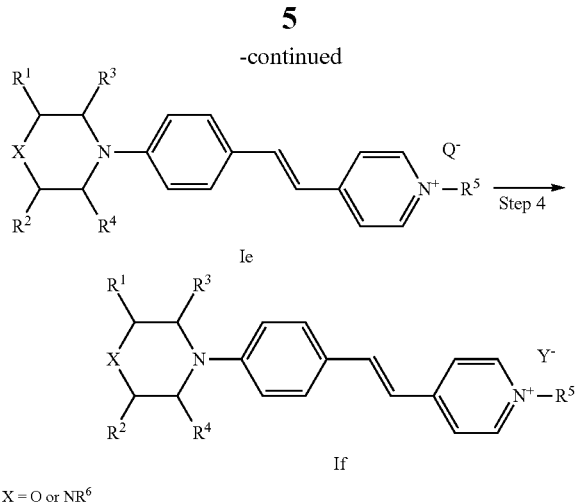

Ie

If

X = O or NR⁶ wherein $R^1$, $R^2$, $R^3$, $R^4$, $R^5$, $R^6$, and $Y^-$ represent the same as those described above.

Step 1

A compound (Ib) with a halide ion $Q^-$ as a counter anion is obtained by allowing 4-picoline (Ia) to react with an alkyl compound having a leaving group, such as alkyl halide, in an ether type solvent such as THF under heating conditions for several hours.

Step 2

A compound (Id) is obtained by allowing a morpholine or a piperazine compound (Ic) to react with, for example, 4-fluorobenzaldehyde in a polar solvent such as DMSO under heating conditions.

Step 3

A compound (Ie) is obtained by allowing the compound (Ib) obtained in the step 1 and the compound (Id) obtained in the step 2 to react with each other in a polar solvent such as methanol under heating conditions.

Step 4

A compound (If) is obtained by allowing the compound (Ie) obtained in the step 3 and an anionic silver salt to react with each other in a polar solvent such as methanol under heating conditions.

The stilbazolium derivative of the present invention can be applied to wavelength conversion elements and terahertz (THz) wave generation devices exhibiting general nonlinear optical material properties because of being a second-order nonlinear optical material.

The stilbazolium derivative of the present invention can also be used as a material for an ingredient for an electric field sensor, an EO element, an optical sampling element, an optical shutter, a high-speed optical switching element, an optical logic gate, an optical transistor, or the like.

Examples of a light source device in which the compound of the present invention is utilized as a light wavelength conversion element include short wavelength laser generation devices, more specifically, a second harmonic generation device.

A light source device 10 (second harmonic generation device) in which the compound of the present invention is utilized as a light wavelength conversion element will be explained with reference to FIG. 1. However, FIG. 1 is only an example, and the light source device is not limited to an embodiment of FIG. 1.

In FIG. 1, reference numeral 1 denotes a laser, reference numeral 2 denotes a lens system, reference numeral 3 denotes a nonlinear optical crystal of the compound of the present invention, reference numeral 4 denotes a fundamental wave cut filter, reference numeral 5 denotes a fundamental wave for the nonlinear optical crystal, and reference numeral 6 denotes a second harmonic.

A laser beam (fundamental wave) having a wavelength of 1310 nm is oscillated using the laser 1 and is converted into a red-colored second harmonic having a wavelength of 655 nm by the nonlinear crystal 3. The wavelength of the laser 1 described above is an example. The wavelength can be selected in a range in which the second harmonic is not greatly absorbed into the nonlinear optical crystal 3.

A crystal for converting a light wavelength need not be a perfect crystal. In the crystal for converting a light wavelength, the compound of the present invention may be aligned so that a second harmonic is generated. In the crystal for converting a light wavelength, the compound of the present invention may also be arranged by applying an electric field or may be aligned on or in resin. The same applies to a case in which the crystal for converting a light wavelength is used in a terahertz wave generation device described below.

Figure 2:
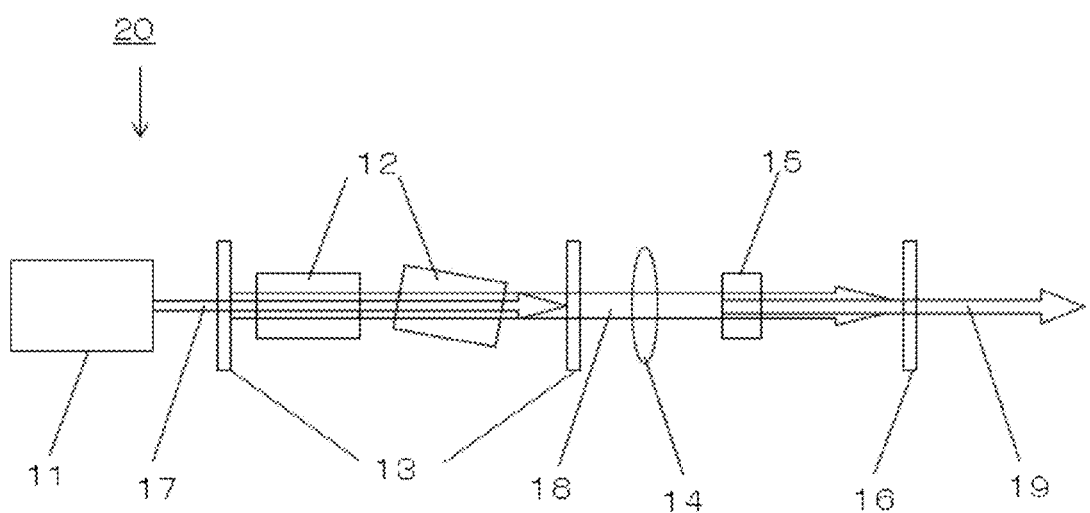
FIG. 2 is a schematic view of a terahertz wave generation device according to one embodiment of the present invention.
Figure 3:
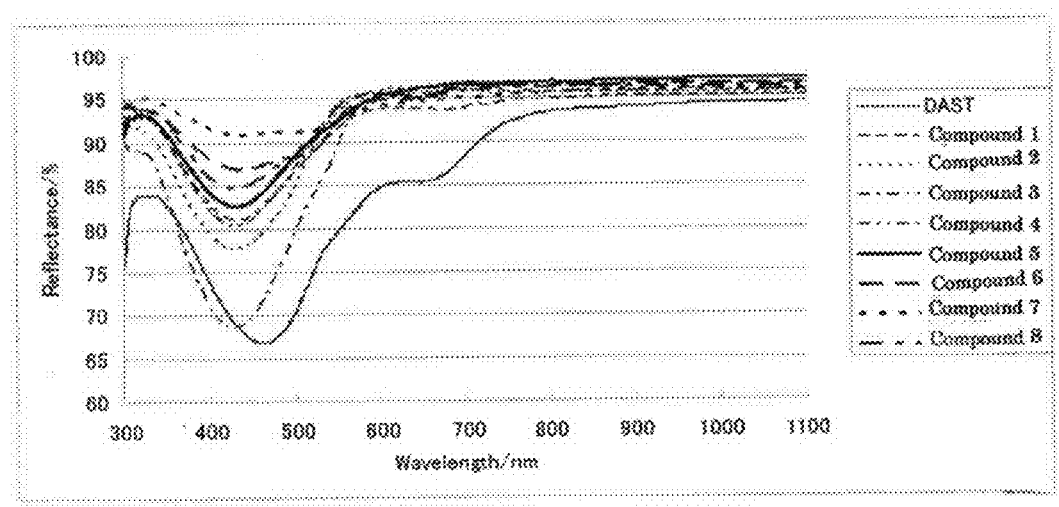
FIG. 3 is a view representing the results of the SHG activity evaluations of DAST and Compounds 1 to 8.

The terahertz wave generation device 20 according to another embodiment of the present invention will be explained below with reference to FIG. 2. However, FIG. 2 is only an example. The terahertz wave generation device is not limited to the embodiment of FIG. 2.

A terahertz wave can be generated by utilizing a difference frequency generation (hereinafter abbreviated as DFG) phenomenon which is a nonlinear optical effect. By allowing two light waves having different wavelengths (frequencies f1 and f2) to incident on a DFG crystal, an electromagnetic wave of f3=|f1-f2| corresponding to the difference frequencies is generated. A THz wave is generated by setting f1 and f2 so that f3 is a THz wave frequency.

An optical parametric oscillator, a Ti sapphire laser, or the like can be used as a dual-wavelength light source.

FIG. 2 is a configuration diagram of a THz wave generation device in which a dual-wavelength optical parametric oscillator and a nonlinear optical crystal are combined. Reference numeral 11 denotes an excitation laser, reference numeral 12 denotes a $KTiOPO_4$ (hereinafter abbreviated as KTP) crystal, reference numeral 13 denotes a mirror, reference numeral 14 denotes a lens system, reference numeral 15 denotes a nonlinear optical crystal of the compound of the present invention, reference numeral 16 denotes a light wave cut filter, reference numeral 17 denotes excitation light, reference numeral 18 denotes dual-wavelength light, and reference numeral 19 denotes a terahertz wave. The dual-wavelength light 18 generated from the optical parametric oscillator comprising mirrors 13 and two KTP crystals 12 having slightly different crystal angles is condensed and allowed to incident on the nonlinear optical crystal 15 of the compound of the present invention by the lens system 14, to generate the terahertz wave 19 due to a nonlinear optical effect.

The crystal of the compound of the present invention may be used in combination with another crystal. For example, the crystal of the compound of the present invention and a crystal of another compound, affixed to each other, may be used as described in Japanese Patent Laid-Open No. 2012-177896.

EXAMPLES

The present invention is specifically explained below with reference to examples. However, embodiments of the present invention are not limited to the examples described below.

Compounds 1 to 8 were synthesized as described below.

Synthesis Example 1

(1-1) Synthesis of 1,4-Dimethylpyridinium Iodide

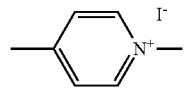

To a solution of 4-picoline (15 g) in THF (160 mL) was added methyl iodide (10 mL) at room temperature. After being stirred for 2 hours at 60° C., a precipitated solid was filtered and dried to thereby obtain a white crystal powder of 1,4-dimethylpyridinium iodide (34.9 g).

$^1$H-NMR (400 MHz, CD$_3$OD) δ: 8.74 (d, J=6.3 Hz, 2H), 7.92 (d, J=6.3 Hz, 2H), 4.36 (s, 3H), 2.68 (s, 3H)

(1-2) Synthesis of 1-Methyl-4-(4-morpholinostyryl)pyridinium Iodide

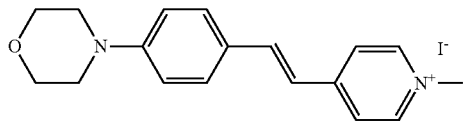 [SMILES: C[n+]1ccc(/C=C/c2ccc(N3CCOCC3)cc2)cc1 ; [I-]]

To a solution of 4-(4-formylphenyl)morpholine (5 g) in methanol (78 mL) was added 1,4-dimethylpyridinium iodide (6.2 g) and piperidine (2.6 mL) at room temperature. After being stirred for 1 day at 45° C., a precipitated solid was filtered and recrystallized from methanol to thereby obtain a red crystal powder of 1-methyl-4-(4-morpholinostyryl)pyridinium iodide (9.3 g).

$^1$H-NMR (400 MHz, CD$_3$OD) δ: 8.58 (d, J=7.3 Hz, 2H), 8.04 (d, J=7.3 Hz, 2H), 7.85 (d, J=16.1 Hz, 1H), 7.65 (d, J=8.8 Hz, 2H), 7.19 (d, J=16.1 Hz, 1H), 7.02 (d, J=8.8 Hz, 2H), 4.25 (s, 3H), 3.83 (t, J=4.9 Hz, 4H), 3.31 (t, J=4.9 Hz, 4H)

(1-3) General Method of Anion Exchange Reaction of 1-Methyl-4-(4-morpholinostyryl)pyridinium Iodide

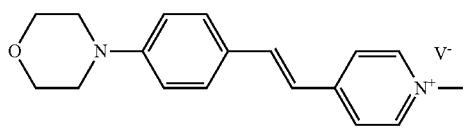

To a solution of 1-methyl-4-(4-morpholinostyryl)pyridinium iodide (1 mmol) in methanol at 60° C. was added an anionic silver salt (1 mmol). After being stirred for 1 day at 60° C., a precipitated silver iodide was filtered off, and methanol in the filtrate was concentrated in vacuo. Recrystallization from methanol gave 1-methyl-4-(4-morpholinostyryl)pyridinium with an anion of interest as a counter anion.

(1-4) Synthesis of 1-Methyl-4-(4-morpholinostyryl)pyridinium 2,4,5-Trichlorobenzenesulfonate

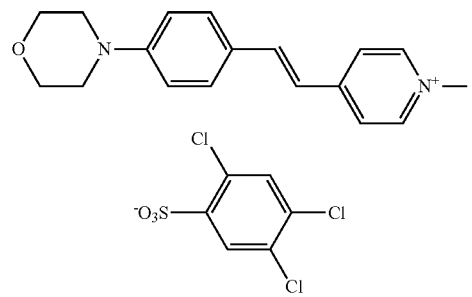

(Compound 1)

On conditions similar to those of the synthesis method in (1-3), 1-methyl-4-(4-morpholinostyryl)pyridinium 2,4,5-trichlorobenzenesulfonate was obtained.

$^1$H-NMR (400 MHz, CD$_3$OD) δ: 8.57 (d, J=6.9 Hz, 2H), 8.10 (s, 1H), 8.02 (d, J=6.9 Hz, 2H), 7.84 (d, J=16.2 Hz, 1H), 7.67 (s, 1H), 7.64 (d, J=8.8 Hz, 2H), 7.18 (d, J=16.2 Hz, 1H), 7.01 (d, J=8.8 Hz, 2H), 4.25 (s, 3H), 3.83 (t, J=4.9 Hz, 4H), 3.31 (t, J=4.9 Hz, 4H)

Synthesis Example 2

(2-1) Synthesis of 4-(cis-2,6-Dimethylmorpholino)benzaldehyde

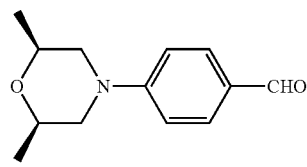 [SMILES: C[C@@H]1CN(c2ccc(C=O)cc2)C[C@H](C)O1]

To a solution of cis-2,6-dimethylmorpholine (23.5 g) in dimethyl sulfoxide (200 mL) was added 4-fluorobenzaldehyde (21 mL) and potassium carbonate (28.2 g) at room temperature. After being stirred for 1 day at 100° C., the reaction mixture was poured into distilled water, and then extracted with ethyl acetate. The organic layers were combined, washed with a saturated aqueous sodium chloride solution, dried over anhydrous magnesium sulfate, filtered and concentrated in vacuo. Purification by silica gel column chromatography (ethyl acetate/hexane) afforded a yellowish white crystal powder of 4-(cis-2,6-dimethylmorpholino)benzaldehyde (33.8 g).

$^1$H-NMR (400 MHz, CDCl$_3$) δ: 9.81 (s, 1H), 7.78 (d, J=9.0 Hz, 2H), 6.97 (d, J=9.0 Hz, 2H), 3.84-3.79 (m, 2H), 3.65 (dd, J=10.8, 2.2 Hz, 2H), 2.60 (dd, J=12.5, 10.8 Hz, 2H), 1.28 (d, J=6.3 Hz, 6H)

(2-2) synthesis of 4-(4-(cis-2,6-Dimethylmorpholino)styryl)-1-methylpyridinium Iodide

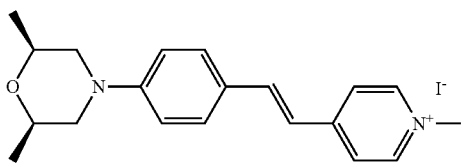

On conditions similar to those of the method for synthesizing 1-methyl-4-(4-morpholinostyryl)pyridinium iodide, 4-(4-(cis-2,6-dimethylmorpholino)styryl)-1-methylpyridinium iodide was obtained from 4-(cis-2,6-dimethylmorpholino)benzaldehyde and 1,4-dimethylpyridinium iodide.

$^1$H-NMR (400 MHz, CD$_3$OD) δ: 8.57 (d, J=7.0 Hz, 2H), 8.03 (d, J=7.0 Hz, 2H), 7.84 (d, J=16.2 Hz, 1H), 7.64 (d, J=8.8 Hz, 2H), 7.18 (d, J=16.2 Hz, 1H), 7.01 (d, J=8.8 Hz, 2H), 4.25 (s, 3H), 3.79-3.71 (m, 4H), 2.45 (dd, J=12.3, 10.4 Hz, 2H), 1.24 (d, J=6.3 Hz, 6H)

(2-3) Synthesis of 4-(4-(cis-2,6-Dimethylmorpholino)styryl)-1-methylpyridinium 2,4,5-Trichlorobenzenesulfonate (Compound 2)

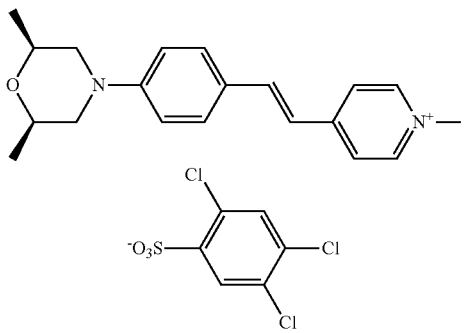

On conditions similar to those of the synthesis method in (1-3), 4-(4-(cis-2,6-dimethylmorpholino)styryl)-1-methylpyridinium 2,4,5-trichlorobenzenesulfonate was obtained.

$^1$H-NMR (400 MHz, CD$_3$OD) δ: 8.56 (d, J=6.9 Hz, 2H), 8.10 (s, 1H), 8.01 (d, J=6.9 Hz, 2H), 7.83 (d, J=16.1 Hz, 1H), 7.67 (s, 1H), 7.63 (d, J=9.0 Hz, 2H), 7.16 (d, J=16.1 Hz, 1H), 7.00 (d, J=9.0 Hz, 2H), 4.25 (s, 3H), 3.79-3.71 (m, 4H), 2.45 (dd, J=12.2, 10.5 Hz, 2H), 1.24 (d, J=6.3 Hz, 6H)

Synthesis Example 3

Synthesis of 4-(4-(cis-2,6-Dimethylmorpholino)styryl)-1-methylpyridinium 4-Fluorobenzenesulfonate (Compound 3)

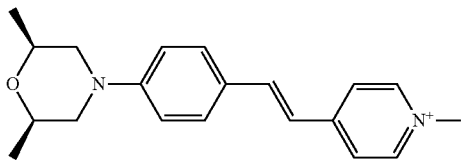 [SMILES: C[C@@H]1CN(c2ccc(/C=C/c3cc[n+](C)cc3)cc2)C[C@H](C)O1 ; [I-]]

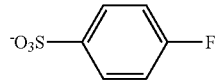

On conditions similar to those of the synthesis method in (1-3), 4-(4-(cis-2,6-dimethylmorpholino)styryl)-1-methylpyridinium 4-fluorobenzenesulfonate was obtained.

$^1$H-NMR (400 MHz, CD$_3$OD) δ: 8.56 (d, J=7.0 Hz, 2H), 8.01 (d, J=7.0 Hz, 2H), 7.87-7.80 (m, 3H), 7.63 (d, J=9.0 Hz, 2H), 7.20-7.10 (m, 3H), 7.01 (d, J=9.0 Hz, 2H), 4.24 (s, 3H), 3.80-3.70 (m, 4H), 2.45 (dd, J=12.2, 10.5 Hz, 2H), 1.24 (d, J=6.3 Hz, 6H)

Synthesis Example 4

(4-1) Synthesis of 1-Methyl-4-(4-(4-methylpiperazinyl)styryl)pyridinium Iodide

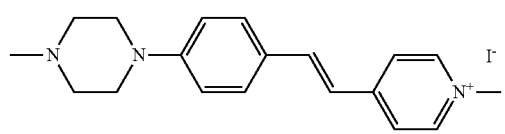

On conditions similar to those of the method for synthesizing 1-methyl-4-(4-morpholinostyryl)pyridinium iodide, 1-methyl-4-(4-(4-methylpiperazinyl)styryl)pyridinium iodide was obtained from 4-(4-methylpiperazinyl)benzaldehyde and 1,4-dimethylpyridinium iodide.

$^1$H-NMR (400 MHz, CD$_3$OD) δ: 8.58 (d, J=6.9 Hz, 2H), 8.03 (d, J=6.9 Hz, 2H), 7.85 (d, J=16.2 Hz, 1H), 7.64 (d, J=8.8 Hz, 2H), 7.19 (d, J=16.2 Hz, 1H), 7.02 (d, J=8.8 Hz, 2H), 4.25 (s, 3H), 3.38 (t, J=5.2 Hz, 4H), 2.61 (t, J=5.1 Hz, 4H), 2.36 (s,3H)

(4-2) Synthesis of 1-Methyl-4-(4-(4-methylpiperazinyl)styryl)pyridinium 4-Chlorobenzenesulfonate (Compound 4)

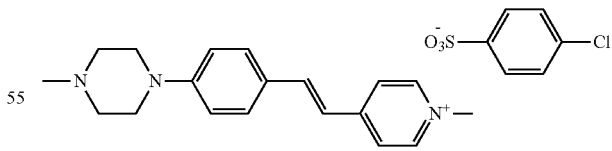

On conditions similar to those of the synthesis method in (1-3), 1-methyl-4-(4-(4-methylpiperazinyl)styryl)pyridinium 4-chlorobenzenesulfonate was obtained.

$^1$H-NMR (400 MHz, CD$_3$OD) δ: 8.56 (d, J=6.9 Hz, 2H), 8.01 (d, J=6.9 Hz, 2H), 7.83 (d, J=16.2 Hz, 1H), 7.80-7.77 (m, 2H), 7.63 (d, J=9.0 Hz, 2H), 7.44-7.39 (m, 2H), 7.17 (d, J=16.2 Hz, 1H), 7.01 (d, J=9.0 Hz, 2H), 4.24 (s, 3H), 3.37 (t, J=5.2 Hz, 4H), 2.61 (t, J=5.2 Hz, 4H), 2.36 (s,3H)

Synthesis Example 5

Synthesis of 1-Methyl-4-(4-(4-methylpiperazinyl)styryl)pyridinium 3-Nitrobenzenesulfonate

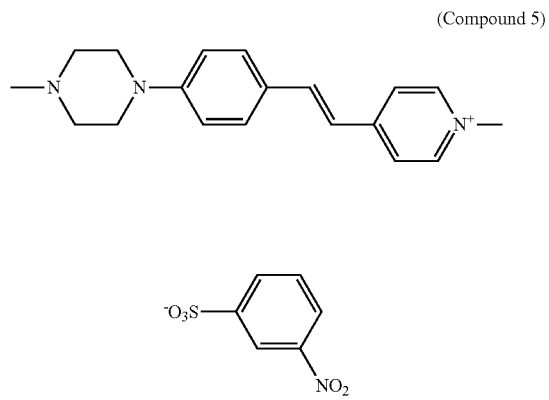

(Compound 5)

On conditions similar to those of the synthesis method in (1-3), 1-methyl-4-(4-(4-methylpiperazinyl)styryl)pyridinium 3-nitrobenzenesulfonate was obtained.

$^1$H-NMR (400 MHz, CD$_3$OD) δ: 8.63-8.60 (m, 1H), 8.57 (d, J=6.9 Hz, 2H), 8.32-8.26 (m, 1H), 8.20-8.15 (m, 1H), 8.02 (d, J=6.9 Hz, 2H), 7.83 (d, J=16.2 Hz, 1H), 7.72-7.65 (m, 1H), 7.63 (d, J=9.0 Hz, 2H), 7.17 (d, J=16.2 Hz, 1H), 7.01 (d, J=9.0 Hz, 2H), 4.25 (s, 3H), 3.38 (t, J=5.1 Hz, 4H), 2.64 (t, J=4.9 Hz, 4H), 2.38 (s, 3H)

Synthesis Example 6

Synthesis of 1-Methyl-4-(4-(4-methylpiperazinyl)styryl)pyridinium 4-Nitrobenzenesulfonate

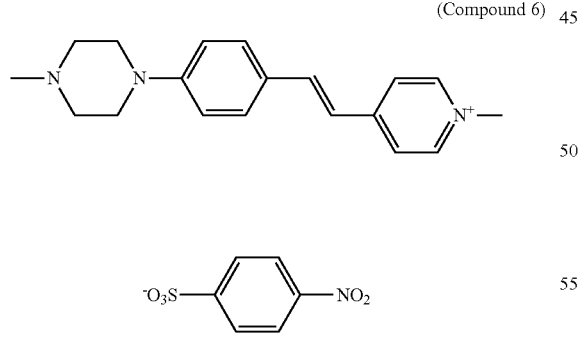

(Compound 6)

On conditions similar to those of the synthesis method in (1-3), 1-methyl-4-(4-(4-methylpiperazinyl)styryl)pyridinium 4-nitrobenzenesulfonate was obtained.

$^1$H-NMR (400 MHz, CD$_3$OD) δ: 8.57 (d, J=7.0 Hz, 2H), 8.31-8.26 (m, 2H), 8.05-8.00 (m, 4H), 7.83 (d, J=16.2 Hz, 1H), 7.63 (d, J=8.9 Hz, 2H), 7.17 (d, J=16.2 Hz, 1H), 7.01 (d, J=8.9 Hz, 2H), 4.25 (s, 3H), 3.37 (t, J=5.2 Hz, 4H), 2.61 (t, J=5.1 Hz, 4H), 2.36 (s, 3H)

Synthesis Example 7

Synthesis of 1-Methyl-4-(4-(4-methylpiperazinyl)styryl)pyridinium Naphthalene-2-sulfonate

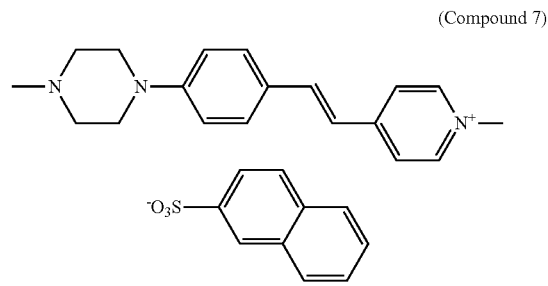

(Compound 7)

On conditions similar to those of the synthesis method in (1-3), 1-methyl-4-(4-(4-methylpiperazinyl)styryl)pyridinium naphthalene-2-sulfonate was obtained.

$^1$H-NMR (400 MHz, CD$_3$OD) δ: 8.57 (d, J=6.9 Hz, 2H), 8.33 (s, 1H), 8.00 (d, J=6.9 Hz, 2H), 7.95-7.85 (m, 4H), 7.80 (d, J=16.2 Hz, 1H), 7.63 (d, J=8.9 Hz, 2H), 7.58-7.50 (m, 2H), 7.17 (d, J=16.2 Hz, 1H), 7.03 (d, J=8.9 Hz, 2H), 4.24 (s, 3H), 3.64-3.52 (m, 4H), 3.26-3.15 (m, 4H), 2.80 (s, 3H)

Synthesis Example 8

Synthesis of 1-Methyl-4-(4-(4-methylpiperazinyl)styryl)pyridinium 2,4,5-Trichlorobenzenesulfonate

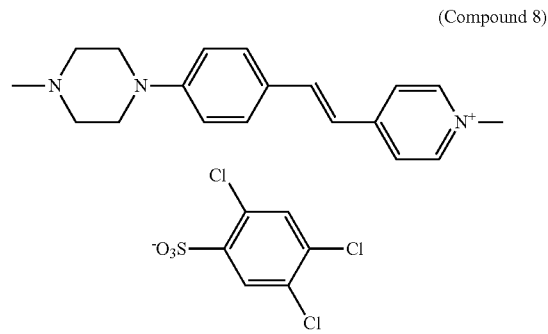

(Compound 8)

On conditions similar to those the synthesis method in (1-3), 1-methyl-4-(4-(4-methylpiperazinyl)styryl)pyridinium 2,4,5-trichlorobenzenesulfonate was obtained.

$^1$H-NMR (400 MHz, CD$_3$OD) δ: 8.56 (d, J=7.0 Hz, 2H), 8.10 (s, 1H), 8.02 (d, J=7.0 Hz, 2H), 7.83 (d, J=16.1 Hz, 1H), 7.67 (s, 1H), 7.63 (d, J=9.0 Hz, 2H), 7.17 (d, J=16.1 Hz, 1H), 7.01 (d, J=9.0 Hz, 2H), 4.25 (s, 3H), 3.37 (t, J=5.1 Hz, 4H), 2.61 (t, J=5.1 Hz, 4H), 2.36 (s, 3H)

Compounds 1 to 8 were evaluated as described below.

[Evaluation of SHG Activity of Microcrystalline Powder]

The microcrystalline powders of the stilbazolium derivatives (DAST and Compounds 1 to 8) were irradiated with a Nd: YAG laser (1064 nm, output of 4 mJ/pulse) to observe emitted green scattered light of 532 nm due to SHG.

[Evaluation of Absorption Edge of Microcrystalline Powder]

The reflectance of a sample produced from a sample powder and barium sulfate was measured to set an absorption edge at a wavelength that was 4% reduced from a baseline (reflectance at 1100 nm where absorption does not occur).

[Evaluation of Laser Tolerance of Microcrystalline Powder]

The microcrystalline powders of DAST and Compound 2 were irradiated with a Nd: YAG laser (1064 nm, output of 6.5 mJ/pulse) to measure SHG intensity with the passage of time.

(Summarization of Evaluation of Compound 1)

When the evaluation of the powder SHG activity of Compound 1 was performed, emitted green scattered light of 532 nm due to SHG was observed. The intensity of the light was 1 time the SHG intensity of that generated from a urea microcrystalline powder in a similar manner. In addition, the absorption edge of the powder crystal was at 547 nm. (The SHG intensity of DAST was 7.6 times, and the absorption edge of DAST was at 720 nm.)

(Summarization of Evaluation of Compound 2)

Figure 4:
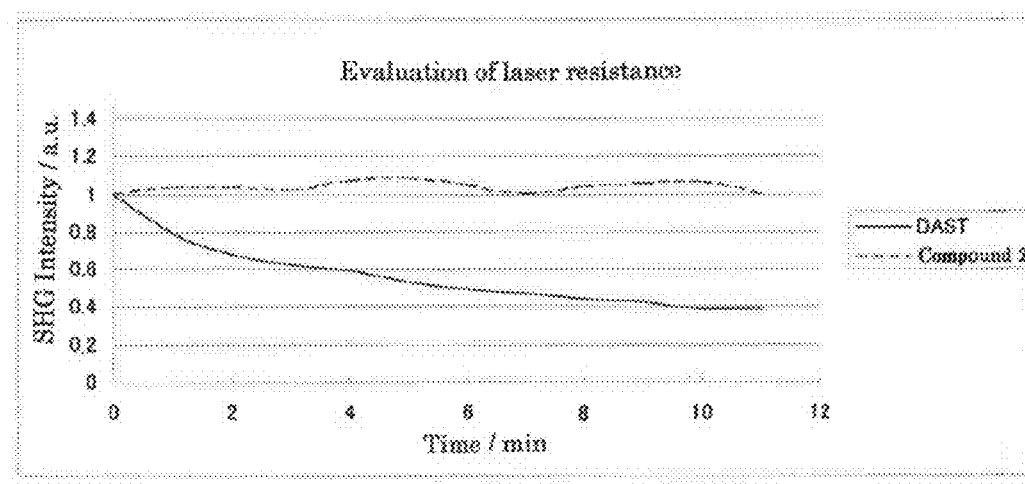
FIG. 4 is a view representing the results of the laser tolerance evaluations of the microcrystalline powders of DAST and Compound 2.

When the evaluation of the powder SHG activity of Compound 2 was performed, emitted green scattered light of 532 nm due to SHG was observed. The intensity of the light was 80.3 times the SHG intensity of that generated from a urea microcrystalline powder in a similar manner. In addition, the absorption edge of the powder crystal was at 534 nm. Unlike DAST, the SHG intensity of Compound 2 was not attenuated with time as illustrated in FIG. 4.

(Summarization of Evaluation of Compound 3)

When the evaluation of the powder SHG activity of Compound 3 was performed, emitted green scattered light of 532 nm due to SHG was observed. The intensity of the light was 0.4 time the SHG intensity of that generated from a urea microcrystalline powder in a similar manner. In addition, the absorption edge of the powder crystal was at 562 nm.

(Summarization of Evaluation of Compound 4)

When the evaluation of the powder SHG activity of Compound 4 was performed, emitted green scattered light of 532 nm due to SHG was observed. The intensity of the light was 12.0 times the SHG intensity of that generated from a urea microcrystalline powder in a similar manner. In addition, the absorption edge of the powder crystal was at 540 nm.

(Summarization of Evaluation of Compound 5)

When the evaluation of the powder SHG activity of Compound 5 was performed, emitted green scattered light of 532 nm due to SHG was observed. The intensity of the light was 6.9 times the SHG intensity of that generated from a urea microcrystalline powder in a similar manner. In addition, the absorption edge of the powder crystal was at 562 nm.

(Summarization of Evaluation of Compound 6)

When the evaluation of the powder SHG activity of Compound 6 was performed, emitted green scattered light of 532 nm due to SHG was observed. The intensity of the light was 7.2 times the SHG intensity of that generated from a urea microcrystalline powder in a similar manner. In addition, the absorption edge of the powder crystal was at 554 nm.

(Summarization of Evaluation of Compound 7)

When the evaluation of the powder SHG activity of Compound 7 was performed, emitted green scattered light of 532 nm due to SHG was observed. The intensity of the light was 0.1 time the SHG intensity of that generated from a urea microcrystalline powder in a similar manner. In addition, the absorption edge of the powder crystal was at 535 nm.

(Summarization of Evaluation of Compound 8)

When the evaluation of the powder SHG activity of Compound 8 was performed, emitted green scattered light of 532 nm due to SHG was observed. The intensity of the light was 18.8 times the SHG intensity of that generated from a urea microcrystalline powder in a similar manner. In addition, the absorption edge of the powder crystal was at 536 nm.

Based on the above, it was found that the compounds of the present invention had the absorption edges shifting to short wavelength sides compared with DAST, and little absorption occurred in a long wavelength region in the visible region. In addition, the compounds 2, 4, 5, 6, and 8 exhibited the SHG intensity equivalent to or greater than that of DAST.

While the invention has been described in detail with reference to preferred embodiments thereof, it will be apparent to one skilled in the art that various changes can be made, and equivalents employed, without departing from the scope of the invention. Each of the aforementioned documents as well as JP2014-129498 is incorporated by reference herein in its entirety.

What is claimed is:

1. A stilbazolium derivative of formula (I):

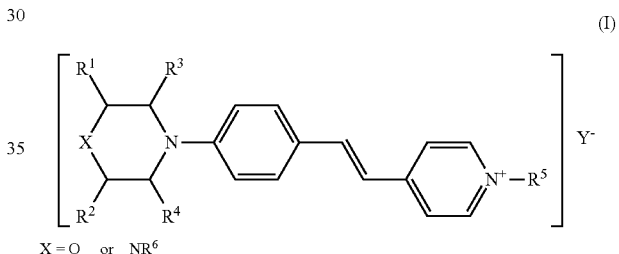

wherein $R^1$, $R^2$, $R^3$, and $R^4$ independently represent hydrogen, halogen, unsubstituted or substituted alkyl, hydroxyl, carboxyl, or amino;

$R^5$ represents hydrogen or unsubstituted or substituted alkyl;

X represents oxygen or $NR^6$ ($R^6$ is hydrogen or unsubstituted or substituted alkyl);

$Y^-$ represents an anion selected from the group consisting of sulfonic acid anions, carboxylic acid anions, hydrogen sulfate ions, nitrate ions, tetrafluoroborate ions, perchlorate ions, perbromate ions, and periodate ions; and in the general formula (I), some or all of hydrogens maybe deuterium wherein said substituted alkyl has a substituent selected from the group consisting of halogen, hydroxyl, ether, carboxyl, nitro, amino, and sulfone.

2. The stilbazolium derivative according to claim 1, wherein $R^1$ and $R^2$ independently represent hydrogen or unsubstituted or substituted alkyl, $R^3$ and $R^4$ represent hydrogen, and $R^5$ represents methyl.

3. The stilbazolium derivative according to claim 1, wherein $Y^-$ is a sulfonic acid anion.

4. The stilbazolium derivative according to claim 2, wherein $Y^-$ is a sulfonic acid anion.

5. A stilbazolium derivative of formula (III):

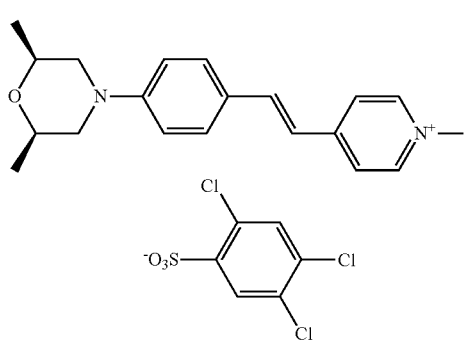

6. A nonlinear optical material comprising the stilbazolium derivative according to claim 1.

7. A nonlinear optical material comprising the stilbazolium derivative according to claim 2.

8. A nonlinear optical material comprising the stilbazolium derivative according to claim 5.

9. A light source device comprising the nonlinear optical material according to claim 6 as a light wavelength conversion element.

10. A light source device comprising the nonlinear optical material according to claim 7 as a light wavelength conversion element.

11. A light source device comprising the nonlinear optical material according to claim 8 as a light wavelength conversion element.

12. A terahertz generation device comprising the nonlinear optical material according to claim 6.

13. A terahertz generation device comprising the nonlinear optical material according to claim 7.

14. A terahertz generation device comprising the nonlinear optical material according to claim 8.

15. A stilbazolium derivative of formula (I):

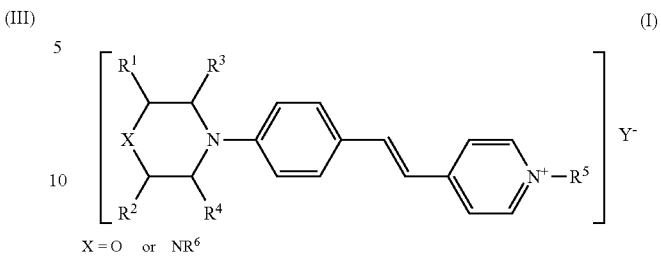

X = O or $NR^6$ wherein $R^1$, $R^2$, $R^3$, and $R^4$ independently represent hydrogen, halogen, unsubstituted or substituted alkyl, hydroxyl, carboxyl, or amino;
$R^5$ represents hydrogen or unsubstituted or substituted alkyl;
X represents oxygen or $NR^6$ ($R^6$ is hydrogen or unsubstituted alkyl);
$Y^-$ represents an anion; and
in the general formula (I), some or all of hydrogens maybe deuterium, wherein said substituted alkyl has a substituent selected from the group consisting of halogen, hydroxyl, ether, carboxyl, ester, nitro, amino, and sulfone, and
wherein $R^1$ and $R^2$ are alkyl when X is oxygen.

16. The stilbazolium derivative according to claim 15, wherein $Y^-$ is a sulfonic acid anion.

17. The stilbazolium derivative according to claim 15, wherein $R^1$ and $R^2$ independently represent hydrogen or unsubstituted or substituted alkyl, $R^3$ and $R^4$ represent hydrogen, $R^5$ represents methyl.

18. A nonlinear optical material comprising the stilbazolium derivative according to claim 15.

19. A light source device comprising the nonlinear optical material according to claim 15 as a light wavelength conversion element.

20. A terahertz generation device comprising the nonlinear optical material according to claim 15.

* * * * *